United States Patent [19]
Zajacek et al.

[11] Patent Number: 6,127,584
[45] Date of Patent: Oct. 3, 2000

[54] BUTANEDIOL PRODUCTION

[75] Inventors: John G. Zajacek, Devon; Wilfred P. Shum, West Chester, both of Pa.

[73] Assignee: Arco Chemical Technology, L.P., Greenville, Del.

[21] Appl. No.: 09/291,737

[22] Filed: Apr. 14, 1999

[51] Int. Cl.$^7$ .................................................... C07C 31/18
[52] U.S. Cl. ............................................................ 568/852
[58] Field of Search ............................................. 568/852

[56] References Cited

U.S. PATENT DOCUMENTS

| | | |
|---|---|---|
| 4,064,145 | 12/1977 | Taylor ................................. 260/346.11 |
| 4,215,077 | 7/1980 | Mataumoto et al. . |
| 4,238,419 | 12/1980 | Matsumoto et al. . |
| 4,590,311 | 5/1986 | Drent ....................................... 568/852 |
| 4,678,857 | 7/1987 | Dureanleau et al. . |
| 5,290,743 | 3/1994 | Chang . |
| 5,504,261 | 4/1996 | Mullin et al. . |

FOREIGN PATENT DOCUMENTS

S52-78809  7/1977  Japan .

*Primary Examiner*—Michael L. Shippen
*Attorney, Agent, or Firm*—William C. Long

[57] ABSTRACT

Allyl alcohol is hydroformated to 1,4-butanediol using a rhodium and trialkyl phosphine catalyst having at least 2 methyl groups, the reaction first being carried out at milder conditions and subsequently at more, severe conditions.

4 Claims, No Drawings

BUTANEDIOL PRODUCTION

BACKGROUND OF THE INVENTION

The present invention provides a process for the production of butanediol from allyl alcohol by hydroformylation at conditions of varying severity; preferably, the same $CO/H_2$ reaction gas mixture is used throughout the process.

FIELD OF THE INVENTION

The production of butanediol from allyl alcohol is a well known and commercially practiced process. See, for example, U.S. Pat. Nos. 4,238,419, 4,678,857, 4,215,077, 5,290,743 and the like. Generally, allyl alcohol is reacted with a $CO/H_2$ gas mixture using a rhodium-phosphine catalyst system to form 4-hydroxy butanal, the 4-hydroxy butanal is separated from the catalyst by water extraction and hydrogenated over a nickel catalyst to form butanediol. See U.S. Pat. No. 5,504,261.

The above reaction sequence involves the use of different catalysts and usually different reaction gas mixtures for each of the reactions. For obvious reasons, it would be advantageous to produce butanediol from allyl alcohol using only a single catalyst system and preferably using only one reaction gas mixture.

It has been reported, for example, in Kokai No. S52-78809 by Kawahito et al that butanediol can be produced from allyl alcohol in a one step reaction system using a rhodium and trialkyl phosphine catalyst system. However, a disadvantage of the process described in S52-78809 is the relatively low ratio of 1,4-butanediol to 2-methyl-1,3 propanediol which is produced.

SUMMARY OF THE INVENTION

In accordance with the present invention, a process is provided for the production of butanediol by reaction of allyl alcohol with CO and $H_2$ using a single catalyst system and preferably a single reaction gas mixture. Initially, the reaction is carried out at relatively mild conditions of temperature and/or pressure which favor the formation of linear reaction products, using a catalyst system comprised of a rhodium compound and an aliphatic phosphine. Subsequently the reaction is continued with the same catalyst system and preferably the same reaction gas mixture, at more severe reaction conditions to form mainly 1,4 butanediol.

Through practice of the invention, disadvantages of the prior procedures of the use of two different catalysts and the separation of intermediate product between reactions are avoided and the ratio of 1,4 butanediol to 2 methyl 1,3 propanediol in the product is significantly enhanced.

As another feature, a further novel reaction is provided wherein allyl alcohol is reacted with CO and $H_2$ using a novel catalyst system comprised of rhodium and an alkyl phosphine of the formula

wherein at least two of R, $R_1$ and $R_2$ is a methyl group. $R_1$ $R_1$ or $R_2$ which is not methyl is a $C_2$–$C_{20}$ alkyl or cycloalkyl group. It has surprisingly been found that the use of these phosphines significantly improves the linear to branched product ratio.

DETAILED DESCRIPTION

In accordance with the invention, allyl alcohol is first reacted with $CO/H_2$ in the presence of a rhodium-trialkyl phosphine catalyst system at relatively mild reaction conditions which strongly favor the formation of linear rather than branched reaction products. Illustrative reaction conditions are temperatures in the range of 60–80° C. and pressures of 30–100 psig; 1/1 molar mixtures of CO and $H_2$ are useful although the ratio can vary considerably and $CO/H_2$ partial pressures of 5–30 psi can be employed. The reaction is conducted at these milder conditions until a predominance of the allyl alcohol has reacted, eg. 60 to 90%, the products being largely 4-hydroxybutanal with some butanediol and branched reaction products. Usually a reaction time of 1 to 4 hours at these milder conditions is adequate.

The reaction is then continued with the same catalyst but at more severe conditions of temperature and pressure, eg. temperatures of 80–140° C. and/or total pressures of 100–1000 psig. The same $CO/H_2$ gas mixture can be used. During reaction at the more severe conditions product butanediol is formed while the high ratio of linear to branched products is substantially retained. Generally reaction times of 1–10 hours at the more severe conditions are appropriate.

In an illustrative embodiment of the invention, allyl alcohol and catalyst, preferably with a suitable solvent are charged to a reactor to which is also introduced the $CO/H_2$ reaction gas mixture. The reactor is heated to reaction temperature and pressurized with the $CO/H_2$ mixture for the desired reaction time to form 4-hydroxy butanol with high selectivity. Preferably agitation is provided.

Thereafter, the temperature of the reaction mixture is increased along with the $CO/H_2$ pressure to the more severe conditions for butanediol formation and these conditions are maintained until the desired conversion to butanediol is achieved.

The product mixture can then be separated either by extraction of the diol products into water or by vacuum distillation of the diols from the reaction mixture.

An important feature of the invention is the fact that by carrying out the reaction first at relatively mild conditions followed by reaction at more severe conditions the selectivity of the overall reaction to 1,4 butanediol, by far the preferred product, is significantly improved with the production of the branched diol 2-methyl 1,3-propanediol reduced. Indeed, through practice of the invention normal diol/branched diol ratios of 3/1 and higher are readily achieved.

The catalyst systems employed are those derived from rhodium or a rhodium compound and trialkylphospine phosphine where two of the alkyl groups are methyl and the third is a $C_2$–$C_{12}$ alkyl group.

A mixture of carbon monoxide and hydrogen is employed; generally mol ratios of hydrogen to carbon monoxide in the range 1:3 to 10:1 are employed, preferably 1:2 to 2:1 and most preferably 1:1. It is especially advantageous to use the same gas mixture throughout the entirety of the reaction although less advantageously the composition of the gas can be varied.

The inventive process can be carried out in batch, continuous or semicontinous mode; continuous is preferred.

It is essential to practice of the invention that initially the reaction between allyl alcohol and the $H_2/CO$ gas mixture be carried out at relatively mild conditions which favor formation of linear hydroxyaldehydes over branched hydroxyaldehydes. Reaction temperatures of 20–80° C., preferably 60–80° C. at total pressures of 30–100 psig (5–30 psig partial pressures of $H_2$/CO, 1/1 mol ratio) and this first stage reaction is continued for 1–4 hours.

Thereafter, the reaction temperature is increased to 80–140° C. and pressure to 100–1000 psig and the reaction is continued at these more severe conditions for 2–4 hours more. The same catalyst is used in both stages and preferably the same $H_2$/CO gas mixture is also employed in both stages.

The reaction product mixture has at least a 3/1 ratio of 1,4 butanediol to 2-methyl 1,3-propanediol and these products are conveniently separated from the catalyst by extraction or vacuum distillation procedures.

Where, in accordance with the invention, a dimethyl phosphine is used, improved linear to branched product ratios are achieved both where the varied severity reaction procedure is employed as above described as well as where a single set of reaction conditions is employed. Phosphines used in this inventive process are trimethyl phosphine and phosphines wherein two of R, $R_1$ and $R_2$ are methyl and the remaining group is $C_2$–$C_{12}$ alkyl, eg dimethyl, octyl phosphine.

The invention can be illustrated by the following examples.

EXAMPLE 1

Into a stainless steel pressure vessel equipped with a magnetic stirrer was charged allyl alcohol (2 g, 34 mmol), toluene (30 g), and catalyst comprised of rhodium dicarbonyl acetylacetonate (0.04 g, 0.16 mmol) and dimethyiodecylphosphine (0.36 g, 1.6mmol). The vessel was flushed with syn gas (CO/$H_2$=1/1), pressurized with the syn gas to 100 psig, and heated to 75° C. The reaction was carried out for four hours at these conditions at which time 75% of the allyl alcohol had reacted to give the following selectivities: 67% 4-hydroxy butanal, 2.6% hydroxy methyl propionaldehyde, 11.8% 1,4-butanediol and 8.3% 2-methyl-1,3-propanediol.

Reaction temperature was then raised to 140° C., reaction pressure to 400 psig, and the reaction continued for an additional two hours. At the end of this time allyl alcohol conversion was 100% and the following yields were obtained: 74% 1,4-butanediol and 13% 2-methyl-1,3-propanediol. A yield of 11% was obtained for isobutanol.

EXAMPLE 2

Example 1 was repeated with a similar feed mixture at 100° C. and 200 psig for 2 hours. At the end of that time, allyl alcohol conversion was 100% and the reaction mixture gave the following yields: 62% 4-hydroxy butanal, 3% hydroxy methyl propionaldehyde, 6% 1,4-butanediol, 8% 2-methyl-1,3-propanediiol, 16% isobutyraldehyde, and 2% isobutanol.

These two examples show the benefits of running the first stage at mild conditions to obtain a higher linear to branched ratio and less $C_4$ by-products.

EXAMPLE 3

To show that other dimethylalkylphosphines can also be used for this one step reaction, example 1 was repeated using a catalyst comprised of rhodium dicarbonyl acetylacetonate (0.04 g, 0.16 mmol) and dimethyl-n-hexylphosphine (0.23 g, 1.6 mmol). After 4 hours at 80° C. and 100 psig, 82% of the allyl alcohol had reacted to give the following selectivities: 65% 4-hydroxy butanal, 2% hydroxy methyl propionaldehyde, 13% 1,4-butanediol, and 9% 2-methyl-1,3-propanediol.

Reaction temperature was then increased to 140° C., reaction pressure to 400 psig, and the reaction continued for another 2 hours. At the end of that time, allyl alcohol conversion was 100% and the reaction product mixture gave a yield of 72% for 1,4-butanediol and 12% for 2-methyl-1,3-propanediol.

EXAMPLE 4 (COMPARATIVE)

The two-stage reaction was carried out using triethylphosphine as ligand. This phosphine ligand has been reported in the literature. Into a stainless steel pressure vessel equipped with a magnetic stirrer was charged allyl alcohol (2 g, 34 mmol), toluene (30 g), and catalyst comprised of rhodium dicarbonyl acetylacetonate (0.04 g, 0.16 mmol) and triethylphosphine (0.18 g, 1.6 mmol). The vessel was flushed with syn gas, pressurized to 100 psig, and heated to 70° C. The reaction was carried out for 2 hours at these conditions at which time 78% of the allyl alcohol had reacted to give the following selectivities: 55% 4-hydroxybutanal, 37% hydroxy methyl propionaldehyde, 2% 1,4-butanediol, and 3% 2-methyl-1,3-propanediol.

Reaction temperature was then increased to 120° C., reaction pressure to 400 psig, and the reaction was continued for another 2 hours. At the end of that time, allyl alcohol conversion was 100%. The yields were 57% 1,4-butanediol and 39% 2-methyl-1,3-propanediol.

EXAMPLE 5 (COMPARATIVE)

Another trialkylphosphine other than triethyphosphine was used for the two-stage reaction. The above example was repeated using a catalyst comprised of rhodium dicarbonyl acetylacetonate (0.04 g, 0.16 mmol) and tri-n-butylphosphine (0.33 g, 1.6 mmol). After 3 hours at 70° C. and 100 psig, 75% of the allyl alcohol had reacted to give the following selectivities: 52% 4-hydroxybutanal, 33% hydroxymethyl propionaldehyde, 5% 1,4-butanediol, and 7% 2-methyl-1,3-propanediol.

Reaction temperature was then increased to 140° C., reaction pressure to 400 psig, and the reaction was continued for another 2 hours. At the end of that time, allyl alcohol conversion was 100%. The yield were 56% 1,4-butanediol and 37% 2-methyl-1,3-propanediol.

It should be noted that it is not practical to carry the reaction to completion under the mild conditions of the first stage in view of the excessive reaction times which would be needed.

What is claimed is:

1. In a process for the production of 1,4-butanediol by hydroformylation of allyl alcohol with a CO/$H_2$ gas mixture using a catalyst comprised of rhodium or a rhodium compound and a trialkyl phosphine having at least 2 methyl groups, the improvement which comprises first carrying out the hydroformylation at 20–80° C. and 30–100 psig until a predominance of allyl alcohol has reacted to form mainly 4-hydroxybutanal, and continuing the reaction at more severe conditions of 80–140° C. and 100–1000 psig to form 1,4-butanediol.

2. The process of claim 1 wherein the phosphine is trimethyl phosphine.

3. The process of claim 1 wherein the hydroformylation is first carried out at 60–80° C. and 30–100 psig until 60–90% of the allyl alcohol is reacted.

4. The process of claim 1 wherein the same CO/$H_2$ gas mixture is used throughout the hydroformylation.

* * * * *